United States Patent
Sahoo et al.

(10) Patent No.: US 12,318,729 B2
(45) Date of Patent: Jun. 3, 2025

(54) ENZYMATIC PHASE TRANSFER SOLVENT FOR $CO_2$/$H_2S$ CAPTURE

(71) Applicant: INDIAN OIL CORPORATION LIMITED, Maharashtra (IN)

(72) Inventors: Prakash Chandra Sahoo, Faridabad (IN); Manoj Kumar, Faridabad (IN); Ravi Prakash Gupta, Faridabad (IN); Suresh Kumar Puri, Faridabad (IN); Sankara Sri Venkata Ramakumar, Faridabad (IN)

(73) Assignee: INDIAN OIL CORPORATION LIMITED, Mumbai (IN)

( * ) Notice: Subject to any disclaimer, the term of this patent is extended or adjusted under 35 U.S.C. 154(b) by 579 days.

(21) Appl. No.: 17/689,865

(22) Filed: Mar. 8, 2022

(65) Prior Publication Data
US 2022/0288531 A1  Sep. 15, 2022

(30) Foreign Application Priority Data
Mar. 9, 2021 (IN) .............................. 202121009850

(51) Int. Cl.
*B01D 53/14* (2006.01)
*B01D 53/85* (2006.01)

(52) U.S. Cl.
CPC ......... *B01D 53/85* (2013.01); *B01D 53/1468* (2013.01); *B01D 53/1475* (2013.01); *B01D 53/1493* (2013.01); *B01D 2252/20* (2013.01); *B01D 2257/304* (2013.01); *B01D 2257/504* (2013.01)

(58) Field of Classification Search
None
See application file for complete search history.

(56) References Cited

U.S. PATENT DOCUMENTS

| | | | |
|---|---|---|---|
| 2007/0237695 A1 | 10/2007 | Hu | |
| 2007/0264180 A1 | 11/2007 | Carrette et al. | |
| 2014/0005995 A1* | 1/2014 | O'Connor | G06F 30/20 |
| | | | 703/9 |

FOREIGN PATENT DOCUMENTS

| | | | | |
|---|---|---|---|---|
| CA | 3030416 | * | 1/2019 | |
| CA | 3092734 A1 | * | 9/2019 | .......... B41M 5/3275 |
| CA | 2827024 A1 | | 7/2020 | |
| CN | 106794414 | * | 5/2017 | |
| EP | 3067108 A1 | | 9/2016 | |
| EP | 3620225 A1 | | 3/2020 | |
| GB | 1567945 A | * | 5/1980 | .......... B01D 53/1475 |
| WO | 2010044836 A1 | | 4/2010 | |
| WO | 2010126694 A1 | | 11/2010 | |
| WO | 2012103653 A1 | | 8/2012 | |
| WO | 2013000953 A2 | | 1/2013 | |
| WO | WO2016030276 | * | 3/2016 | |
| WO | 2017035667 A1 | | 3/2017 | |
| WO | WO2020262805 | * | 12/2020 | |

OTHER PUBLICATIONS

Li, Lucy et al. "A Review of Corrosion in Aircraft Structures . . . ". SEnsors. 21. 2908. (2021) (Year: 2021).*
Encyclopedia Britannica. "Gravimetric analysis". https://www.britannica.com/science/gravimetric-analysis 2024. (Year: 2024).*
Pinto et.al "Evaluation of a phase change solvent for CO2 capture: Absorption and desorption tests." International Journal of Greenhouse Gas Control 28 (2014): 318-327, Jul. 7, 2014.
Jiang et al., "Phase splitting agent regulated biphasic solvent for efficient CO2 capture with a low heat duty" Treatment and Resource Recovery, Environmental Science & Technology, May 22, 2020.
Ye et al., "A novel biphasic solvent with tunable phase separation for CO2 capture: role of water content in mechanism, kinetics, and energy penalty" Remediation and Control Technologies, Environmental Science & Technology, Mar. 21, 2019.

* cited by examiner

*Primary Examiner* — Sheng H Davis
(74) *Attorney, Agent, or Firm* — Maschoff Brennan (57) ABSTRACT

The present invention relates to a novel phase transfer solvent composition for enhanced $CO_2$ and/or $H_2S$ capture from flue gas and biogas having various gaseous compositions. Further, the present invention provides a process of preparing the phase transfer solvent composition of the present invention.

11 Claims, 3 Drawing Sheets

ENZYMATIC PHASE TRANSFER SOLVENT FOR CO$_2$/H$_2$S CAPTURE

TECHNICAL FIELD

The present disclosure relates generally to the field of Environmental Sciences and Technology. In particular, the present invention relates to a novel phase transfer solvent composition for enhanced CO$_2$ and/or H$_2$S capture from flue gas and biogas having various gaseous compositions. More specifically, the disclosure relates to improved enzymatic and solvent systems, which upon CO$_2$/H$_2$S capture forms selective phases with higher CO$_2$/H$_2$S loading efficiency and low regeneration energy over the existing solvent systems.

BACKGROUND ART

CO$_2$ emission from post-combustion streams is the major anthropogenic source of greenhouse gas responsible for global climate change. With the ever-growing industrial demand of fossil fuel use, CO$_2$ accumulation within the atmosphere is predicted to increase substantially. To reduce the impact of the CO$_2$ emissions from multiple sources, capture of CO$_2$ has been advocated.

Among the post combustion carbon capture technologies, chemical absorption using aqueous amine solutions with thermal regeneration of the solvent is the most developed and applied technology for CO$_2$ capture. Most of the energy required for CO$_2$ capture in amine scrubbing systems is used for regenerating the solvent, which makes the amine scrubbing very cost intensive for their commercial application. The development of new solvents or solvent blends is an important way of reducing the energy demand in amine scrubbing plants.

New class of solvent systems known as phase transitional solvents (PTS), have attracted increased interest for their potential to substantially reduce both energy use and equipment costs for CO$_2$ capture. These solvents are homogeneous (single-phase) solvents before CO$_2$ is loaded and upon CO$_2$ absorption or a temperature shift, they form multiple phases:

a CO$_2$-enriched phase and a CO$_2$-lean phase. Because only the CO$_2$-enriched liquid phase is used for solvent regeneration, the mass of solvent that requires regeneration is decreased. Consequently, the heat required to heat the solvent (sensible heat) is reduced.

There are few CO$_2$ absorption and desorption using phase transfer solvent have been disclosed in the prior art.

US20070237695A1 relates to a method and system for gas separation using a liquid absorbent absorbing one of the gases to be separated, where the absorbent spontaneously separates into a phase rich in the absorbed gas, and a phase lean in the absorbed gas. The active agent in the not identified but preferred agents is indicated to be selected from the group consisting of alkaline salts, ammonium, alkanolamines, amines, amides and combinations thereof.

WO2013000953A2 described a liquid, aqueous CO$_2$ absorbent comprising two or more amine compounds, where the aqueous solution of amines having absorbed CO$_2$ is not, or only partly miscible with an aqueous solution of amines not having absorbed CO$_2$, where at least one of the amines is a tertiary amine, and where at least one of the amines is a primary and/or a secondary amine, wherein the tertiary amine is DEEA and the primary and/or secondary amine(s) is (are) selected from DAB, DAP, DiAP, DMPDA, HEP, or the tertiary amine is DIPAE, or N-TBDEA and primary and/or secondary amine(s) is (are) selected from DAB, DAP, DiAP, DMPDA, HEP, MAPA, and MEA, and a method for CO$_2$ capture using the CO$_2$ absorbent.

WO2010126694A1 relates to a method for de-acidizing an acid gas mixture using an absorbent comprising an amine dissolved in a mixture at a first concentration. After absorption of the acid gas, the absorbent forms a concentrated-amine phase, this is separated from the remainder of the absorbent and is introduced into a regeneration unit, whereas the remaining of the absorbent is recycled back into the absorption unit. A series of organic solvents are mentioned as the solvent, together with water and aqueous solutions. Organic solvents are mentioned as preferred solvents. The only exemplified absorbents are MEA in isooctane, which spontaneously forms a concentrated amine phase containing MEA and the reaction product of MEA and CO$_2$, and an aqueous carbonate solution, which forms insoluble bicarbonate on absorption of CO$_2$.

WO2010044836A1 relates to a method for de-acidizing an acid gas mixture using an absorbent comprising a carrier phase and an organic phase that is immiscible with the carrier phase. Introduction of an organic solvent as described herein is unwanted, mixed solvent systems add complexity to the systems.

WO2017035667A1 The present description relates to recombinant or engineered carbonic anhydrase polypeptides, variants, and functional derivatives thereof, having improved properties that make them advantageous for use in CO$_2$ capture operations (e.g., CO$_2$ capture solvents, alkaline pH, and/or elevated temperatures), as well as polynucleotides and vectors encoding same. The present description also relates to methods, processes and systems for CO$_2$ capture which make use of the recombinant or engineered carbonic anhydrase polypeptides, variants, and functional derivatives thereof.

CA2827024A1 describes a carbonic anhydrase system and processes are disclosed. The system has a reaction chamber, liquid inlet, gas inlet, liquid outlet and gas outlet, and uses carbonic anhydrase on or in substrates in suspension in the liquid for catalyzing a reaction of CO$_2$ into bicarbonate and hydrogen ions to obtain a treated gas and an ion-rich solution.

Ye et. al "Novel biphasic solvent with tunable phase separation for CO$_2$ capture: Role of water content in mechanism, kinetics, and energy penalty." Environmental science & technology 53, no. 8 (2019): 4470-4479 describes a phase transfer system composed of triethylenetetramine (TETA) and 2-(diethylamino) ethanol (DEEA) blends.

Pinto et.al "Evaluation of a phase change solvent for CO$_2$ capture: Absorption and desorption tests." International Journal of Greenhouse Gas Control 28 (2014): 318-327 describes a blend of a tertiary amine (DEEA) and a diamine (MAPA) for CO$_2$ capture.

Jiang et.al, Environmental Science & Technology 54, no. 12 (2020): 7601-7610 describes a phase splitting agent-regulated biphasic solvent for efficient CO$_2$ capture with a low heat duty.

The drawbacks of the above-said process are:

Low CO$_2$ loading capacity and high desorption energy.

Low cyclic capacity during subsequent absorption and desorption cycles.

Described prior art has provision for removal CO$_2$ and not suitable for H$_2$S removal.

Simultaneous CO$_2$ and H$_2$S removal essential for various processes including biogas purification.

Selective phase formation for CO$_2$ and H$_2$S is not possible.

Sluggish kinetics for CO$_2$/H$_2$S capture.

Longer time for phase formation.

High concentration amine solution required.

Higher amine degradation.

Higher circulation rates are required for removal of $CO_2$ to desired levels.

The present address the problem existing in the art by providing a novel phase transfer solvent composition for enhanced $CO_2$ and/or $H_2S$ capture from flue gas and biogas having various gaseous compositions. More specifically, the disclosure relates to improved enzymatic and solvent systems, which upon $CO_2/H_2S$ capture forms selective phases with higher $CO_2/H_2S$ loading efficiency and low regeneration energy over the existing solvent systems. The disclosure further provides a phase transfer solvent composed of a primary amine/secondary amine, a tertiary amine, a hyperthermophilic enzyme, thermoregulatory enzyme stabilizer, phase splitting agent, phase stabilizing agent and thermo-conductive nanofluid, where the combination synergistically improves $CO_2/H_2S$ loading and have a phase separation behaviour with energy-efficient regeneration for $CO_2/H_2S$.

Moreover, suitable combination of enzyme and solvent synergistically results in low corrosion, improved cyclic capacity and low viscosity alteration. The whole process is "stand alone" The possible advantages of the present inventions, but not limited to, are:

Efficient enzymatic phase transfer process.

Enzyme activation depends on temperature i.e. at low temperature enzyme catalyze the absorption process whereas at higher temperature, the same enzyme catalyses $CO_2$ desorption.

Fast phase separation improves the $CO_2/H_2S$ separation throughput.

Selective phase for $CO_2$ and $H_2S$ observed, which resulted selective regeneration of acid gases.

Low sensible heat requirement for solvent regeneration.

Objective:

An aim of the present invention is to provide a novel phase transfer solvent composition for enhanced $CO_2$ and/or $H_2S$ capture from flue gas and biogas having various gaseous compositions.

Another objection of the present invention is to provide a process of preparing the phase transfer solvent composition of the present invention.

SUMMARY OF THE INVENTION

The invention provides a phase transfer solvent composed of a primary amine/secondary amine, a tertiary amine, a hyperthermophilic enzyme, thermoregulatory enzyme stabilizer, phase splitting agent, phase stabilizing agent and thermo-conductive fluid, where the combination synergistically improves $CO_2/H_2S$ loading and exhibit a phase separation behavior with energy-efficient regeneration for $CO_2/H_2S$ compared to conventional solvent systems. Further, the present invention provides a process of preparing the phase transfer solvent composition of the present invention.

BRIEF DESCRIPTION OF THE DRAWINGS

These and other features, aspects, and advantages of the present invention will become better understood when the following detailed description is read with reference to the accompanying drawings in which like characters represent like parts throughout the drawings wherein.

DETAILED DESCRIPTION

For the purpose of promoting an understanding of the principles of the invention, reference will now be made to the embodiments illustrated in the figures and specific language will be used to describe the same. It will nevertheless be understood that no limitation of the scope of the invention is thereby intended, such alterations and further modifications in the illustrated system, and such further applications of the principles of the invention as illustrated therein being contemplated as would normally occur to one skilled in the art to which the invention relates. Unless otherwise defined, all technical and scientific terms used herein have the same meaning as commonly understood by one of ordinary skilled in the art to which this invention belongs. The system, methods, and examples provided herein are illustrative only and not intended to be limiting.

The terminology and structure employed herein is for describing, teaching and illuminating some embodiments and their specific features and elements and does not limit, restrict or reduce the spirit and scope of the invention.

The invention discloses a novel phase transfer solvent composition for enhanced $CO_2$ and/or $H_2S$ capture from flue gas and biogas having various gaseous compositions. More specifically, the disclosure relates to improved enzymatic and solvent systems, which upon $CO_2/H_2S$ capture forms selective phases with higher $CO_2/H_2S$ loading efficiency and low regeneration energy over the existing solvent systems. The disclosure further provides a phase transfer solvent composed of a primary amine/secondary amine, a tertiary amine, a hyperthermophilic enzyme, thermoregulatory enzyme stabilizer, phase splitting agent, phase stabilizing agent and thermo-conductive fluid, where the combination synergistically improves $CO_2/H_2S$ loading and exhibit a phase separation behaviour with energy-efficient regeneration for $CO_2/H_2S$.

In an aspect of the present invention, inventors provide a phase transfer solvent composition for enhanced $CO_2$ and/or $H_2S$ capture from flue gas and biogas having various gaseous compositions, comprising:

a) a compound having minimum one primary and/or one secondary amine groups;

b) a compound having minimum one tertiary amine;

c) a hyperthermophilic enzyme;

d) a thermoregulatory enzyme stabilizer;

e) a phase splitting agent;

f) a phase stabilizing micellar agent;

g) a thermo-conductive fluid; and h) 200-600 ml of demineralized water per litre to make up the volume;

wherein said solvent composition synergistically improves $CO_2/H_2S$ loading and exhibit a phase separation behaviour with energy-efficient regeneration for $CO_2/H_2S$.

In an embodiment, said compound having minimum one primary and/or one secondary amine groups are selected from group consisting of Monoethanolamine, Diethanolamine, Triethanolamine, Monomethylethanolamine, 2-(2-aminoethoxy)ethanol, Aminoethylethanolamine, Ethylenediamine (EDA), Diethylenetriamine (DETA), Triethylenetetramine (TETA). Tetraethylenepentamine (TEPA), 2-amino 2methyl-1-proponal (AMP), 2-(ethyamino)-ethanol (EAE), 2-(methylamino)-ethanol (MAE), 2-(diethylamino)-ethanol (DEAE), diethanolamine (DEA), diisopropanolamine (DIPA), methylaminopropylamine (MAPA), 3-aminopropanol (AP), 2,2-dimethyl-1,3-propanediamine (DMPDA), 3-amino-1-cyclohexylaminopropane (ACHP), diglycola mine (DGA), 1-amino-2-propanol (MIPA), Isobutyl amine, 2-amino-2-methyl-ipropanol, 2-(2-aminoethylamino)ethanol, 2-amino-2-hydroxymethyl-i,3-propanediol, N-methyldiethanolamine, dimethylmonoethanolamine, diethylmonoethanolamine, triisopropanolamine and triethanolamine), trimethylamine, triethylamine, tripropylamine, tributylamine, dimethylethylamine, dimethylpropylamine, dimethylbutylamine, diethylmethylamine, diethylpropylamine, diethylbutylamine, N,N-diisopropylmethylamine, N-ethyldiisopropylamine, N,N-dimethyl ethyl amine, N,N-diethylbutylamine, 1,2-dimethylpropylamine, N,N-diethylmethylamine, N,N-dimethylisopropylamine, 1,3-dimethylbutylamine, 3,3-dimethylbutylamine, N,N-dimethylbutylamine, N-methyl-1, 3-diaminopropane, Piperazine and triethylenetetramine or a combination thereof.

In another embodiment, said compound having minimum one primary and/or one secondary amine groups has a concentration range of 20-50 wt % in phase transfer solvent and depend on the feed gas $CO_2$ concentration.

In yet another embodiment, compounds having minimum one tertiary amine includes but not limited to diethylethanolamine, dimethylethanolamine, diisopropanolamine, methyldiethanolamine, triethanolamine, 2-Amino-2-MethylPropan-1-ol, bis (2-dimethylaminoethyl) ether, tetramethyl-1, 2-ethanediamine, tetramethyl-3-propane, N-methyl diethanolamine, Dimethylethanolamine Tetramethyl-6-hexanediamine, 1,3,5-Trimethylhexahydro-1,3,5-triazine N,N,N',N'-Tetramethyl-2-butene-1,4-diamine, Pentamethyldipropylenetriamine, N,N-diethylethanolamine, N,N-dimethylbutylamine, 3-(methyloamino)propylamine, or a combination thereof.

In a further embodiment, compound having minimum one tertiary amine has a concentration range from 20-30 wt % in phase transfer solvent and depends on the feed gas $CO_2$ concentration.

In an embodiment, said hyperthermophilic enzyme is Carbonic Anhydrase (CA) obtained from a source selected from the group consisting of *Bacillus thermoleovorans* IOC-S3 (MTCC 25023) and/or *Pseudomonas fragi* IOC S2 (MTCC 25025), and/or *Bacillus stearothermophilus* IOC S1 (MTCC 25030) and/or *Arthrobacter* sp. IOC-SC-2 (MTCC 25028).

In another embodiment, said hyperthermophilic enzyme has concentration range of 10-50 ppm of the total phase transfer solvent.

In yet another embodiment, said thermoregulatory enzyme stabilizer is in the concentration range of 2-4 ppm per 1000 U/mg of enzyme.

In a further embodiment, said phase splitting agent is selected from sulfolane, tetrahydrothiophene-1-oxide, butadiene sulfone, and a combination thereof.

In an embodiment, said phase splitting agent has a concentration range from 1-5% in phase transfer solvent and depends on the tertiary amine concentration.

In another embodiment, said phase stabilizing micellar agent is selected from the group consisting of N-[2-[(2-Aminoethyl) amino]ethyl]-9-octadecenamide (AMEO), n-Benzalkonium chloride (BAC), $C_nH_{(2n+1)}$—COO $(CH_2CH_2O)_{12}CH_3$, Polyoxythylene alkyl ether, n-Alkyltrimethyl ammonium surfactant, Potassium alkanoate, Dodecylpyridinium bromide, Octylglucoside, Sodium dodecyl sulfate, trans-Cinnamaldehyde, Sodium bis-(2-ethylhexyl)-sulfosuccinate, Cetylpyridinium chloride, Primary alcohol ethoxylate, Polyoxyethylene nonyl phenyl ether, Polyethylene glycol esters, Linoleate, dodecylamine or a combination thereof.

In yet another embodiment, said phase stabilizing micellar agent has a concentration range from 50-70 ppm in phase transfer solvent.

In a further embodiment, said thermo-conductive fluid comprises nano-fluids of $SiO_2$, $Al_2O_3$, and $TiO_2$, $Al_2O_3$, $TiCl_2$/Nano-γ-$Al_2O_3$, $CoFe_2O_4$, magnetic $Fe_3O_4$, $Ga_2O_3$, functional silica, colloidal $In_2O_3$, ZnO, CoO, $MnO_2$, $Fe_3O_4$, PbS, $MFe_2O_4$ (M=Fe, Co, Mn, Zn), Lewis acid $ZrO_2$, silica boron sulfuric acid nanoparticles, Ni metal nanoparticles loaded on the acid-base bifunctional support ($Al_2O_3$), $Co_3O_4$ nanoparticles, oxide or metallic nano particle.

In an embodiment, said thermo-conductive fluid has a size in the range of between 10-50 nm and the concentration of the thermo-conductive fluid particle side ranges between 6-8 ppm.

In a second aspect of the present invention, the inventors provide a process of preparing the phase transfer solvent composition as claimed in claim 1, wherein said process comprises the steps of:
Step-1: Preparing modified hyperthermophilic enzyme;
Step-2: Preparing phase transfer solvent system; and
Step-3: Evaluating the obtained phase transfer solvent.

In an embodiment, said Step 1 comprises:
a) isolating hyperthermophilic enzyme from microbial strain under suitable condition;
b) preparing thermoregulatory enzyme stabilizer using selective oligonucleotide metal complex; and
c) complexing thermoregulatory enzyme stabilizer prepared in step (b) with hyperthermophilic enzyme in step (a) to obtain the modified hyperthermophilic enzyme.

In another embodiment, said condition for isolation of hyperthermophilic enzyme is as follows:
inducing enzyme expression by the addition of 0.5 mM $ZnSO_4$ in a cell culture and growing the cells overnight at 55° C.;
lysing the cells by the use of a Bead-Beater and removing cell debris by centrifugation;
pooling fractions containing the enzyme and dialyzing the same against 0.1 M Tris/$SO_4$ at pH 7.5;
extracting the enzyme from the nutrient medium by 40% ammonium sulfate precipitation;
wherein the extracted enzyme has concentration of 100-150 mg/ml with an p-NPA activity of 1800-2000 U/mg, able to be stored at −20° C. for two years without loss of activity, able to be stored at room temperature when immobilized can be stored for 1 year with 95-98% of initial activity and has a thermal stability of 100-110° C.

In yet another embodiment, the thermoregulatory enzyme stabilizer is prepared using metal complexation with selective oligonucleotide.

In a further embodiment, the oligonucleotide is a single stranded hexamer oligonucleotide with a minimum of two thiosine bases such as TTACTA, TTAATC, TTGATA, and TTGCTC or a combination thereof and the metal salt used for complexation is a chloride salt of Fe, Co, Cu and Ni or a combination thereof.

In an embodiment, the concentration of oligonucleotides and metal salts were of 5-10 pmol/μl and 50-100 pmol/μl, respectively for the synthesis of thermoregulatory enzyme stabilizer.

In another embodiment, complexation of thermoregulatory enzyme stabilizer and hyperthermophilic enzyme is due to hydrogen bonding.

In yet another embodiment, complexation of thermoregulatory enzyme stabilizer and hyperthermophilic enzyme is carried out by mixing 2 ppm of thermoregulatory enzyme stabilizer per 1000 U/mg of hyperthermophilic enzyme in presence of phosphate buffer (50 mM) of pH 6-6.5.

In a further embodiment, the activity of hyperthermophilic enzyme is enhanced after complexation with thermoregulatory enzyme stabilizer.

In an embodiment, complexation of thermoregulatory enzyme stabilizer and hyperthermophilic enzyme catalyses $CO_2$ absorption within a temperature range of 0-40° C.

In another embodiment, complexation of thermoregulatory enzyme stabilizer and hyperthermophilic enzyme catalyses $CO_2$ desorption in the temperature range of 50-110° C.

In yet another embodiment, the complexation of thermoregulatory enzyme stabilizer and hyperthermophilic enzyme can be used in free flow, fixed bed, rotating bed and any other configuration.

In a further embodiment, the complexation of thermoregulatory enzyme stabilizer and hyperthermophilic enzyme will be affective for phase transformation solvent, homogeneous solvent or any other form of solvent used for $CO_2$ capture.

In an embodiment, said Step 2 comprises:
a) preparing amine solution with compounds having minimum one primary and/or one secondary amine groups by mixing said solution for 1-2 hours;
b) adding compounds having at least one tertiary amine groups to the above step (a) with constant stirring;
c) adding a phase splitting agent to the above step (b) and mixing till formation of a homogeneous phase;
d) adding modified hyperthermophilic enzyme prepared in step-1c as defined in the present invention;
e) adding a phase stabilizing agent to the composition in the above step (d);
f) after 2 hours of constant stirring of the mixture composition obtained in the above step (e), adding a thermo-conductive fluid to the same to obtain the final phase transfer solvent composition which homogeneous at room temperature.

In another embodiment, said Step 3 comprises:
a) passing of $CO_2/H_2S$ gas to the phase transfer solvent at different condition;
b) allowing the separation of rich and lean $CO_2/H_2S$ loading phases;
c) separating the $CO_2/H_2S$ lean phase and recycling the lean phase into the absorber;
d) withdrawing the $CO_2/H_2S$ rich stream and passing the same into the stripper column for regeneration of the $CO_2/H_2S$;
e) After regeneration, allowing the $CO_2/H_2S$ lean solvent stream to the absorber;
f) measuring gas ($CO_2/H_2S$) loading in the solvent by gravimetric method and pressure drop experiment;
g) determining the cyclic capacity;
h) monitoring viscosity after $CO_2/H_2S$ loading for a period of 200 cycles and observing no change in viscosity;
i) monitoring corrosion for 0-100 days in a stainless vessel by analysis the leaching metal ion in the solvent;
j) monitoring vapor pressure; and
k) conducting recyclability study of phase transfer solvent.

In yet another embodiment, the $CO_2$ concentration ranges from 0.02% to 99%, preferably 0.02% to 90% in the source gas and the $H_2S$ concentration ranges from 0.001% to 5%.

In a further embodiment, the $CO_2/H_2S$ phases differ in density, the rich phase is heavier than the $CO_2/H_2S$ lean phase, allowing the phases to be separated by density, gravity or centrifugation apparatus.

In an embodiment, the separation of phases happens in 1-10 s for both $CO_2$ and $H_2S$ gas feed.

In another embodiment, the $CO_2$ and $H_2S$ rich phase is routed to different stripper column to selectively separate high pure $H_2S$ and $CO_2$.

In yet another embodiment, the regeneration temperature ranges from 75° C. to 95° C.

In a further embodiment, $CO_2$ sources are carbon dioxide-containing flue gas, process gas or gas from bio-methanation.

In an embodiment, the resulting gas is passed through the solvent medium through in any suitable device forming the fine dispersion of gas which result in an increase in contact area, said gas is sparged in micro-bubble or nano-bubble size.

In another embodiment, the pressure of $CO_2/H_2S$ ranges from ambient to 10 bar and temperature ranges between 20-50° C.

The following examples and experiments are for illustrative purposes only and not intended to limit the scope of this disclosure.

EXAMPLES

Material and Methods:

The typical concentration of components used in phase transfer solvent of the present invention are given in the following table-1

TABLE 1

Detail concentration of different components of phase transfer solvent

| Component | Concentration in phase transfer solvent |
|---|---|
| Compounds having minimum one primary and/or one secondary amine groups. | 20-50 wt % |
| Compounds having minimum one Tertiary amine | 20-30 wt % |
| Hyperthermophilic enzyme (1800-2000 U/mg) | 10-50 ppm |
| Thermoregulatory enzyme stabilizer | 2-4 ppm per 1000 U/mg of enzyme |
| Phase splitting agent | 1-5 wt % |
| Phase stabilizing micellar agent | 50-70 ppm |
| Thermo-conductive fluid | 6-8 ppm |
| DM water | To make up the volume |

Example 1: $CO_2$ Capture by Novel Phase Transfer Solvent

1. Preparation of Modified Hyperthermophilic Enzyme

The hyperthermophilic enzyme was extracted from Bacillus stearothermophilus IOC S1 (MTCC 25030). Initially, the microbes were grown in media having composition (in g/l) 6.0 g of $Na_2HPO_4$, 3.0 g of $KH_2PO_4$, 1.0 g of $NH_4Cl$, 0.5 g of NaCl, 0.014 g of $CaCl_2$, 0.245 g of $MgSO_4 \cdot 7H_2O$, 10 mg of thiamine hydrochloride and 10 g of starch, and with 1 mM IPTG at 55° C. and 6.5 pH.

Enzyme expression was induced by the addition of 0.5 mM $ZnSO_4$ and the cells were grown overnight at 55° C. The cells were lysed by the use of a Bead-Beater and cell debris was removed by centrifugation. The pooled fractions containing the enzyme were dialyzed against 0.1 M $Tris/SO_4$ at pH 7.5. The enzyme was extracted from the nutrient medium by ammonium sulfate precipitation method. The purity of the enzyme was monitored by SDS/PAGE by comparing it with commercially available enzyme. The concentration of extracted enzyme was found to be 145 mg/ml by UV-Vis assay with p-NPA activity of 1955 U/mg. The enzyme was stored at RT.

For the preparation of thermoregulatory enzyme stabilizer, oligonucleotid of sequence TTACTA was synthesized. Oligonucleotides (100 mM oligonucleobases) and Iron chloride (100 mM) were prepared in HEPES buffer (10 mM, 1 mM magnesium nitrate, and pH 7.2).

Oligonucleotides and Iron chloride were then mixed with equal volumes. The final concentration of both oligonucleobases and iron chloride were both 50 mM. After equilibration at 30° C. for 10 minutes, the stable Fe-oligonucleotides complex was obtained and confirmed by appearance of sharp ligand to metal charge transfer spectra at 622 nm. The complex was collected by centrifugation with an rpm 8000 for 10 min.

2 ppm of thermoregulatory enzyme stabilizer was added to isolated hyperthermophilic enzyme (1L) having an activity of activity of 1955 U/mg. The solution was placed in the shaker overnight at 120 rpm at 60° C. resulting the modified hyperthermophilic enzyme. The characteristic of modified hyperthermophilic enzyme is given in table-2 Comparison of the activity for hyperthermophilic enzyme and modified hyperthermophilic enzyme using $CO_2$ or p-NPA as substrate is given in Table-2.

TABLE 2

Activity of biocatalyst before and after modification

| Biocatalyst | Activity |
| --- | --- |
| Hyperthermophilic enzyme | 1955 U/mg |
| Modified hyperthermophilic enzyme | 3569 U/mg |
| Hyperthermophilic enzyme@100° C. for 720 h | 1912 U/mg |
| Modified hyperthermophilic enzyme@100° C. for 720 h | 3522 U/mg |

2. Preparation of Phase Transfer Solvent System

In a 2 L flask 5M diethylethanolamine and N,N-Dimethyl-1,3-diaminopropane (2M) were mixed for 2 h. To the solution 0.2M sulfolane was added drop-wise with 2 ml/min with constant stirring. To the same solution 50 ppm of modified hyperthermophilic enzyme was inserted followed by 70 ppm of phase stabilizing micellar agent (Sodium dodecyl sulfate). After 2 h of constant stirring 8 ppm of thermo-conductive fluid ($Fe_2O_4$ having average particle side 24 nm) was inserted to obtain the final phase transfer solvent system. The mixture is homogeneous at Room temperature.

3. Evaluation of Novel Phase Transfer Solvent

A known volume and mass (500 ml) of the solvent was weighed into the reactor and a synthetic mixture of $CO_2$ (35%) and balance $N_2$ was inserted to the solution, with a flow of 20 ml/min, was bubbled into the solvent. After bubbling through the solution, the gas stream was cooled on-line through two condensers placed on top of each other and the condensate was directly returned to the reactor. The purified gas was collected for GC analysis. The $CO_2$ loading was studied by gravimetric method under equilibrium condition. It was observed that upon $CO_2$ loading, the $CO_2$-rich phase formed in the bottom constitute 22% of the total solvent volume. The $CO_2$ rich phase was separated after used for desorption tests in stripping column.

TABLE 3

Table represents % of phase separation with respect to time.

| Time (s) | $CO_2$ Lean phase (%) | $CO_2$ Rich phase (%) |
| --- | --- | --- |
| 0 | No Separation | No Separation |
| 2 | 68 | 32 |
| 5 | 71 | 29 |
| 10 | 78 | 22 |
| 20 | 78 | 22 |
| 100 | 79 | 21 |
| 500 | 79 | 21 |

4. $CO_2$ Loading Capacity in Rich and Lean Amine

Figure 1:
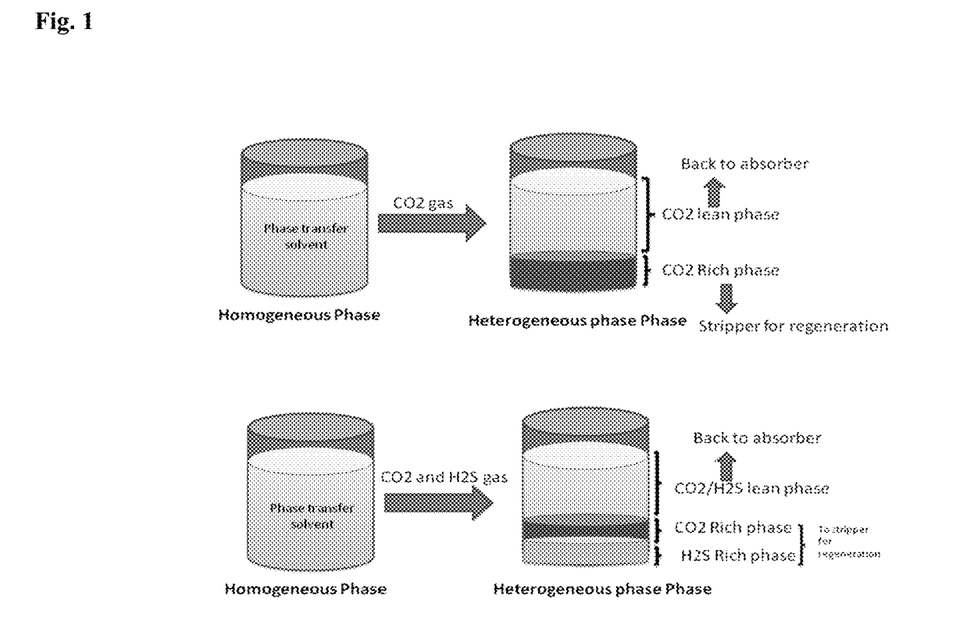
FIG. 1 illustrates Schematic representation of phase separation of solvent upon gas absorption.
Figure 2:
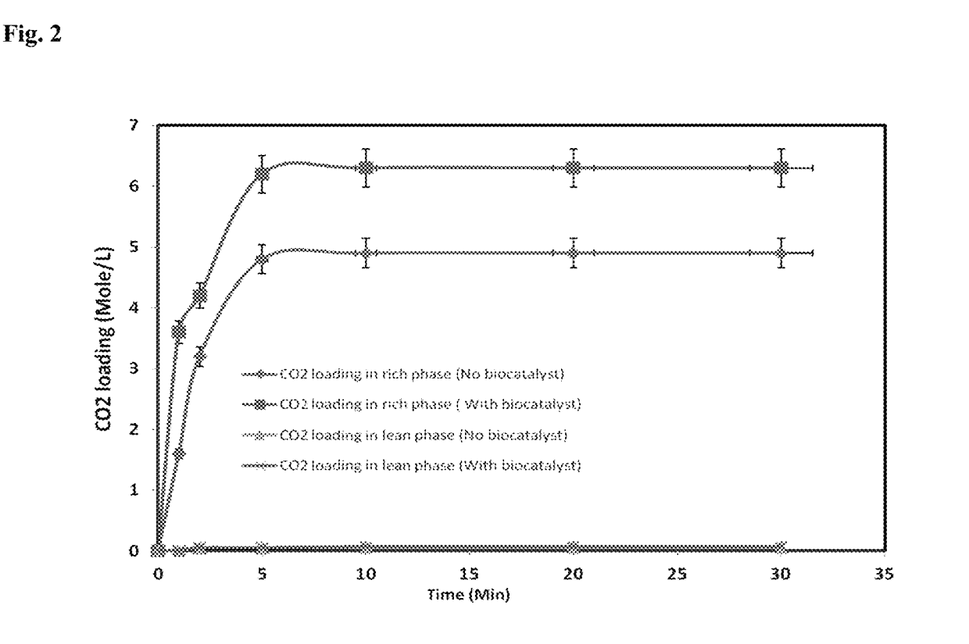
FIG. 2 illustrates $CO_2$ loading in $CO_2$ lean and $CO_2$ rich phase with and without biocatalyst.
Figure 3:
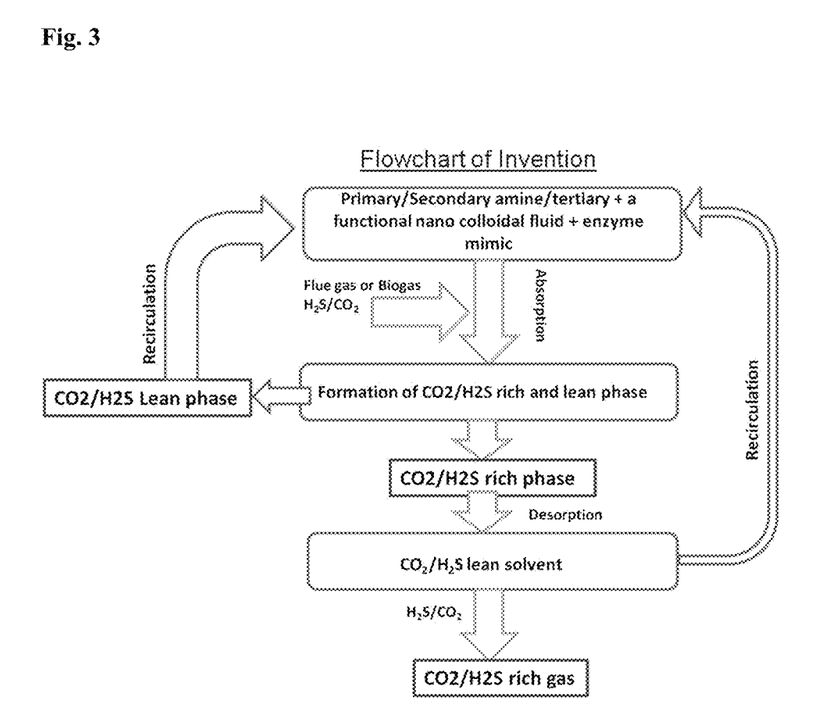
FIG. 3 illustrates flowchart of complete process for $CO_2/H_2S$ capture using phase transfer solvent.

FIG. 2 provides the comparative $CO_2$ loading in phase transfer solvent with and without biocatalyst. As shown in the figure, the biocatalyst significantly increase the $CO_2$ loading in $CO_2$ rich phase (6.31 mol/L) compared to that of rich solvent without biocatalyst (4.9 Mol/L).

TABLE 4

The time-dependent $CO_2$ uptake with various components of phase transfer solvents measured at 30° C. and 1 atm pressure using the gravimetric method.

| Code | Components | $CO_2$ loading (Mol/L) | Observation of phase separation behaviors |
| --- | --- | --- | --- |
| A | Diethylethanolamine | 2.3 | No Phase separation |
| B | N,N-Dimethyl-1, 3-diaminopropane | 1.1 | No Phase separation |
| C | Dulfolane | ND | No Phase separation |
| D | Hyperthermophilic enzyme | 0.04 | No Phase separation |
| E | Thermoregulatory enzyme stabilizer-(Fe-TTACTA) | ND | No Phase separation |
| F | phase stabilizing micellar agent (Sodium dodecyl sulfate) | ND | No Phase separation |
| G | thermo-conductive fluid | ND | No Phase separation |
| A + B | | 3.48 | No Phase separation |
| A + C | | 2.5 | No Phase separation |
| A + B + C | | 3.9 | Phase separation |
| A + B + D | | 4.2 | No Phase separation |
| A + B + E | | 3.45 | No Phase separation |
| A + B + F | | 3.42 | No Phase separation |
| A + B + C + D | | 4.9 | Phase separation |
| A + B + C + E | | 3.86 | Phase separation |
| A + B + C + F | | 1.91 | Phase separation |
| B + C + D + F | | 2.31 | No Phase separation |
| A + B + C + D + E + F + G (Novel phase transfer solvent) | | 6.31 | Phase separation |

TABLE 5

Desorption of $CO_2$ rich phase transfer solvent at 85-95° C.

| Phase transfer solvent | Desorption (%) |
| --- | --- |
| Phase transfer solvent-Without bio | 68% |

TABLE 5-continued

Desorption of $CO_2$ rich phase transfer solvent at 85-95° C.

| Phase transfer solvent | Desorption (%) |
|---|---|
| catalyst | |
| phase transfer solvent-With Hyperthermophilic enzyme | 71% |
| phase transfer solvent-With Modified Hyperthermophilic enzyme | 94% |

TABLE 6

Cyclic capacity refers to the difference between lean and rich loading of a solvent. In this study, the lean loading was defined as $CO_2$ loading corresponding to $CO_2$ at equilibrium partial pressure of 0.05 kPa at 85-90° C.

| Solvent | Lean loading (mol $CO_2$/kg-solv) | Rich loading (mol $CO_2$/kg-solv) | Cyclic capacity (mol $CO_2$/kg-solv) |
|---|---|---|---|
| MEA | 1.68 | 2.52 | 0.84 |
| Phase transfer solvent | 0.07 | 6.3 | 6.23 |

Example-2: Biogas Purification by Phase Transfer Solvent

Preparation of Phase Transfer Solvent

The phase transfer solvent was prepared based on the protocol mentioned step-1, 2 and 3 of the example-1.

Biogas of composition (75% Methane, 5000 ppm $H_2S$ balance $CO_2$) was used for the study. The flow rate of solvent was kept 20 ml/min, was bubbled into the solvent. After bubbling through the solution, the gas stream was cooled on-line through two condensers placed on top of each other and the condensate was directly returned to the reactor. The purified gas was collected for GC analysis. The $CO_2$/$H_2S$ loading was studied by gravimetric method under equilibrium condition. It was observed that upon $CO_2$ loading, the $CO_2$-rich phase formed in the bottom constitute 21.5% of the total solvent volume, H2S rich phase was 7% of the total volume. The $CO_2$ and $H_2S$ rich phase were separated after used for desorption tests in stripping column.

TABLE 7

Table represents % of phase separation with respect to time.

| Time (s) | $CO_2$/$H_2S$ Lean phase (%) | $CO_2$ Rich phase (%) | $H_2S$ Rich phase (%) |
|---|---|---|---|
| 0 | No Separation | No Separation | No Separation |
| 2 | 62 | 29 | 9 |
| 5 | 65 | 28 | 7 |
| 10 | 71 | 22 | 7 |
| 20 | 71.5 | 22 | 6.5 |
| 100 | 72.5 | 21 | 6.5 |
| 500 | 72.5 | 21 | 6.5 |

TABLE 8

Effect of biocatalyst in $CO_2$ and $H_2S$ loading

| Time | $CO_2$ loading in rich phase (No biocatalyst) | $CO_2$ loading in rich phase (With biocatalyst) | $H_2S$ loading in rich phase (No biocatalyst) | $H_2S$ loading in rich phase (With biocatalyst) |
|---|---|---|---|---|
| 0 | 0 | 0 | 0 | 0 |
| 1 | 1.6 | 3.6 | 0.7 | 1.1 |
| 2 | 3.2 | 4.2 | 0.9 | 1.7 |
| 5 | 4.8 | 6.1 | 1.01 | 2.2 |
| 10 | 4.9 | 6.2 | 1.05 | 2.3 |
| 20 | 4.9 | 6.2 | 1.05 | 2.3 |
| 30 | 4.9 | 6.2 | 1.05 | 2.3 |

TABLE 9

| Solvent system | Input Biogas composition | Output methane recovery |
|---|---|---|
| Phase transfer solvent | $CH_4$ (50 V %) | $CH_4$ (99.8 V %) |
| | $CO_2$ (49.7 V %) | $CO_2$ (0.2 V %) |
| | $H_2S$ (3000 ppm) | $H_2S$ (N.D) |
| | $CH_4$ (60 V %) | $CH_4$ (99.9 V %) |
| | $CO_2$ (39.6 V %) | $CO_2$ (0.1 V %) |
| | $H_2S$ (4000 ppm) | $H_2S$ (N.D) |
| | $CH_4$ (70 V %) | $CH_4$ (99.9 V %) |
| | $CO_2$ (29.9 V %) | $CO_2$ (0.1 V %) |
| | $H_2S$ (1000 ppm) | $H_2S$ (N.D) |
| | $CH_4$ (80 V %) | $CH_4$ (99.9 V %) |
| | $CO_2$ (19.5 V %) | $CO_2$ (0.1 V %) |
| | $H_2S$ (5000 ppm) | $H_2S$ (N.D) |

It will thus be seen that the objects set forth above, among those made apparent from the preceding description, are efficiently attained, and since certain changes may be made in the constructions set forth without departing from the spirit and scope of the invention, it is intended that all matter contained in the above description shall be interpreted as illustrative and not in a limiting sense. The invention has been described with reference to preferred and alternate embodiments. Modifications and alterations will become apparent to those skilled in the art upon reading and understanding the detailed discussion of the invention provided herein. This invention is intended to include all such modifications and alterations insofar as they come within the scope of the present invention. These and other modifications of the preferred embodiments as well as other embodiments of the invention will be obvious from the disclosure herein, whereby the foregoing descriptive matter is to be interpreted merely as illustrative of the invention and not as a limitation.

Finally, to the extent necessary to understand or complete the disclosure of the present invention, all publications, patents, and patent applications mentioned herein are expressly incorporated by reference therein to the same extent as though each were individually so incorporated.

The invention claimed is:
1. A process for capturing $CO_2$ and/or $H_2S$ from a source gas using a phase transfer solvent, the process comprising:
preparing the phase transfer solvent;
passing the source gas comprising $CO_2$ and/or $H_2S$ through the phase transfer solvent;
separating a $CO_2$ and/or $H_2S$ rich stream and a $CO_2$ and/or $H_2S$ lean stream;
recycling the $CO_2$ and/or $H_2S$ lean stream through an absorber;

withdrawing the $CO_2$ and/or $H_2S$ rich stream and passing into a stripper column for regeneration of the $CO_2$ and/or $H_2S$, wherein regeneration temperature ranges from 75° C. to 95° C.; and measuring $CO_2$ and/or $H_2S$ loading in the phase transfer solvent by gravimetric method and pressure drop experiment to determine cyclic capacity;

wherein preparing the phase transfer solvent comprises:
preparing an amine solution by mixing one primary amine and one secondary amine for 1-2 hours;
adding at least one tertiary amine with constant stirring;
adding a phase splitting agent and mixing till formation of a homogeneous phase;
preparing a modified hyperthermophilic enzyme;
adding the modified hyperthermophilic enzyme to the homogeneous phase;
adding a phase stabilizing agent and continuously stirring for 2 hours; and
adding a thermo-conductive fluid to obtain the phase transfer solvent, wherein preparing the modified hyperthermophilic enzyme comprises:
isolating a hyperthermophilic enzyme from a microbial strain;
preparing a thermoregulatory enzyme stabilizer using a selective oligonucleotide metal complex, wherein the selective oligonucleotide metal complex comprises an oligonucleotide and a metal salt, wherein the oligonucleotide is a single stranded hexamer oligonucleotide with a minimum of two thiosine bases comprising TTACTA, TTAATC, TTGATA, TTGCTC or a combination thereof and the metal salt is a chloride salt of Fe, Co, Cu, Ni or a combination thereof and wherein the oligonucleotide is in a concentration of 5-10 pmol/µl, and the metal salt is in a concentration of 50-100 pmol/µl; and
complexing the thermoregulatory enzyme stabilizer with the hyperthermophilic enzyme to obtain the modified hyperthermophilic enzyme, wherein complexation of the thermoregulatory enzyme stabilizer and the hyperthermophilic enzyme is due to hydrogen bonding and is carried out by mixing 2 ppm of the thermoregulatory enzyme stabilizer per 1000 U/mg of the hyperthermophilic enzyme in presence of a phosphate buffer (50 mM) of pH 6-6.5, wherein the modified hyperthermophilic enzyme is affective for a phase transformation solvent, or a homogeneous solvent used for $CO_2$ capture.

2. The process as claimed in claim 1, wherein complexing the thermoregulatory enzyme stabilizer and hyperthermophilic enzyme catalyses $CO_2$ absorption within a temperature range of 50-110° C., wherein complexing is carried out in a free flow reactor, a fixed bed reactor, or a rotating bed reactor.

3. The process as claimed in claim 1, wherein the primary and secondary amines are selected from the group consisting of Monoethanolamine, Diethanolamine, Triethanolamine, Monomethylethanolamine, 2-(2-aminoethoxy) ethanol, Aminoethylethanolamine, Ethylenediamine (EDA), Diethylenetriamine (DETA), Triethylenetetramine (TETA), Tetraethylenepentamine (TEPA), 2-amino 2methyl-1-proponal (AMP), 2-(ethyamino)-ethanol (EAE), 2-(methylamino)-ethanol (MAE), 2-(diethylamino)-ethanol (DEAE), diethanolamine (DEA), diisopropanolamine (DIPA), methylaminopropylamine (MAPA), 3-aminopropanol (AP), 2,2-dimethyl-1,3-propanediamine (DMPDA), 3-amino-1-cyclohexylaminopropane (ACHP), diglycola mine (DGA), 1-amino-2-propanol (MIPA), Isobutyl amine, 2-amino-2-methyl-ipropanol, 2-(2-aminoethylamino) ethanol, 2-amino-2-hydroxymethyl-i,3-propanediol, N-methyldiethanolamine, dimethylmonoethanolamine, diethylmonoethanolamine, triisopropanolamine and triethanolamine), trimethylamine, triethylamine, tripropylamine, tributylamine, dimethylethylamine, dimethylpropylamine, dimethylbutylamine, diethylmethylamine, diethylpropylamine, diethylbutylamine, N,N-diisopropylmethylamine, N-ethyldiisopropylamine, N,N-dimethylethylamine, N,N-diethylbutylamine, 1,2-dimethylpropylamine, N,N-diethylmethylamine, N,N-dimethylisopropylamine, 1,3-dimethylbutylamine, 3, 3-dimethylbutylamine, N,N-dimethylbutylamine, N-methyl-1,3-diaminopropane, Piperazine, triethylenetetramine, and a combination thereof; wherein the primary amine and the secondary amine are in a concentration range of 20-50 wt % in phase transfer solvent.

4. The process as claimed in claim 1, wherein the at least one tertiary amine is selected from the group consisting of diethylethanolamine, dimethylethanolamine, diisopropanolamine, methyldiethanolamine, triethanolamine, 2-Amino-2-MethylPropan-1-ol, bis(2-dimethylaminoethyl) ether, tetramethyl-1, 2-ethanediamine, tetramethyl-3-propane, N-methyl diethanolamine, Dimethylethanolamine Tetr amethyl-6-hexanediamine, 1,3,5-Trimethylhexahydro-1,3, 5-triazine N,N,N',N'-Tetramethyl-2-butene-1,4-diamine, Pentamethyldipropylenetriamine, N,N-diethylethanolamine, N,N-dimethylbutylamine, 3-(methyloamino) propylamine, and a combination thereof; and, wherein the at least one tertiary amine is in a concentration range from 20-30 wt % in phase transfer solvent.

5. The process as claimed in claim 1, wherein the hyperthermophilic enzyme is Carbonic Anhydrase (CA) obtained from a source selected from the group consisting of *Bacillus thermoleovorans* IOC-S3 (MTCC 25023), *Pseudomonas fragi* IOC S2 (MTCC 25025), *Bacillus stearothermophilus* IOC S1 (MTCC 25030), and *Arthrobacter* sp. IOC-SC-2 (MTCC 25028), and wherein the hyperthermophilic enzyme is in a concentration range of 10-50 ppm of the phase transfer solvent; and wherein the thermoregulatory enzyme stabilizer is in a concentration range of 2-4 ppm per 1000 U/mg of the hyperthermophilic enzyme.

6. The process as claimed in claim 1, wherein the phase splitting agent is selected from the group consisting of sulfolane, tetrahydrothiophene-1-oxide, butadiene sulfone, and a combination thereof, wherein the phase splitting agent is in a concentration range from 1-5% of the phase transfer solvent.

7. The process as claimed in claim 1, wherein the thermo-conductive fluid is selected from the group consisting of nano-fluids of $SiO_2$, $Al_2O_3$, and $TiO_2$, $Al_2O_3$, $TiCl_2$/Nano-$\gamma Al_2O_3$, $CoFe_2O_4$, magnetic $Fe_3O_4$, $Ga_2O_3$, functional silica, colloidal $In_2O_3$, ZnO, CoO, $MnO_2$, $Fe_3O_4$, PbS, $MFe_2O_4$(M=Mn, Zn), Lewis acid $ZrO_2$, silica nanoparticles, Ni nanoparticles loaded on the acid-base bifunctional support ($Al_2O_3$), $Co_3O_4$ nanoparticles, metal oxides, and metallic nano particles and wherein the thermo-conductive fluid has a particle size in a range of 10-50 nm and a concentration in a range of 6-8 ppm.

8. The process as claimed in claim 1, wherein the $CO_2$ concentration ranges from 0.02% to 99%, and the $H_2S$ concentration ranges from 0.001% to 5% in the source gas, wherein the separation of phases happens in 1-10 s for both $CO_2$ and $H_2S$ source gas.

9. The process as claimed in claim 1, wherein the source gas comprising $CO_2$ is carbon dioxide-containing flue gas, process gas or gas from bio-methanation.

10. The process as claimed in claim 1, wherein the source gas is passed through the phase transfer solvent as a fine dispersion having a micro or a nano bubble size.

11. The process as claimed in claim 1, wherein the isolation of the hyperthermophilic enzyme comprises:
inducing enzyme expression by adding 0.5 mM $ZnSO_4$ in a cell culture and growing cells overnight at 55° C.;
lysing the cells by using a Bead-Beater and removing cell debris by centrifugation;
pooling enzyme fractions and dialyzing against 0.1 M $Tris/SO_4$ at pH 7; and
extracting the enzyme from nutrient medium by precipitating with 40% ammonium sulfate;
wherein the extracted enzyme has a concentration in a range of 100-150 mg/ml with a p-NPA activity of 1800-2000 U/mg, wherein the enzyme is characterized to be stored at −20° C. for two years without loss of activity, and is characterized to be stored at room temperature when immobilized for 1 year with 95-98% of initial activity, and has a thermal stability of 100-110° C.

* * * * *